United States Patent [19]

Spielmann

[11] Patent Number: 5,432,087
[45] Date of Patent: Jul. 11, 1995

US005432087A

[54] APPARATUS HAVING ROTATABLE PLANAR TRAYS FOR CULTURING MICROORGANISMS

[76] Inventor: Richard Spielmann, Rue d'Hérinnes 43, B-7850 Enghien, Belgium

[21] Appl. No.: 64,098

[22] PCT Filed: Nov. 28, 1991

[86] PCT No.: PCT/BE91/00084
§ 371 Date: May 20, 1993
§ 102(e) Date: May 20, 1993

[87] PCT Pub. No.: WO92/09681
PCT Pub. Date: Jun. 11, 1992

[30] Foreign Application Priority Data

Nov. 29, 1990 [BE] Belgium .............................. 09001137

[51] Int. Cl.⁶ ..................... C12M 1/14; C12M 1/10; C12M 3/04; C12N 5/00
[52] U.S. Cl. ........................... 435/312; 435/240.23; 435/284; 435/285; 435/286; 435/310
[58] Field of Search ............... 435/240.23, 284, 285, 435/286, 310, 312

[56] References Cited

U.S. PATENT DOCUMENTS

| | | | |
|---|---|---|---|
| 3,839,155 | 10/1974 | McAleer et al. | 435/285 |
| 3,925,165 | 12/1975 | Muller | 435/312 X |
| 4,310,630 | 1/1982 | Girard et al. | 435/312 X |
| 4,912,058 | 3/1990 | Mussi et al. | 435/285 |
| 5,270,205 | 12/1993 | Rogalsky | 435/312 X |

FOREIGN PATENT DOCUMENTS

| | | |
|---|---|---|
| 51646 | 7/1966 | Belgium . |
| 2354554 | 6/1977 | France . |
| 2055397 | 3/1981 | United Kingdom . |
| 8800235 | 1/1988 | WIPO . |

*Primary Examiner*—David M. Naff
*Attorney, Agent, or Firm*—Ostrager, Chong & Flaherty

[57] ABSTRACT

Adherent or non-adherent microorganisms with or without microcarriers are cultured in an apparatus having rotatable planar trays that dip in and out of culture medium and momentarily retain culture medium due to rims along edges of the trays on both sides. The trays are in a housing that is substantially cylindrical and elongated along a longitudinal axis. The trays are arranged longitudinally to the longitudinal axis with spacing between the trays. The trays can be attached substantially radially to and around a shaft extending coaxially inside the housing, attached to both the shaft and the housing or attached to the housing without a shaft. Attachment is at one or two longitudinal edges of the trays. The shaft can be hollow and have a wall with openings. During culturing, the trays can be rotated in one direction 180° and then rotated through 180° in an opposite direction.

5 Claims, 5 Drawing Sheets

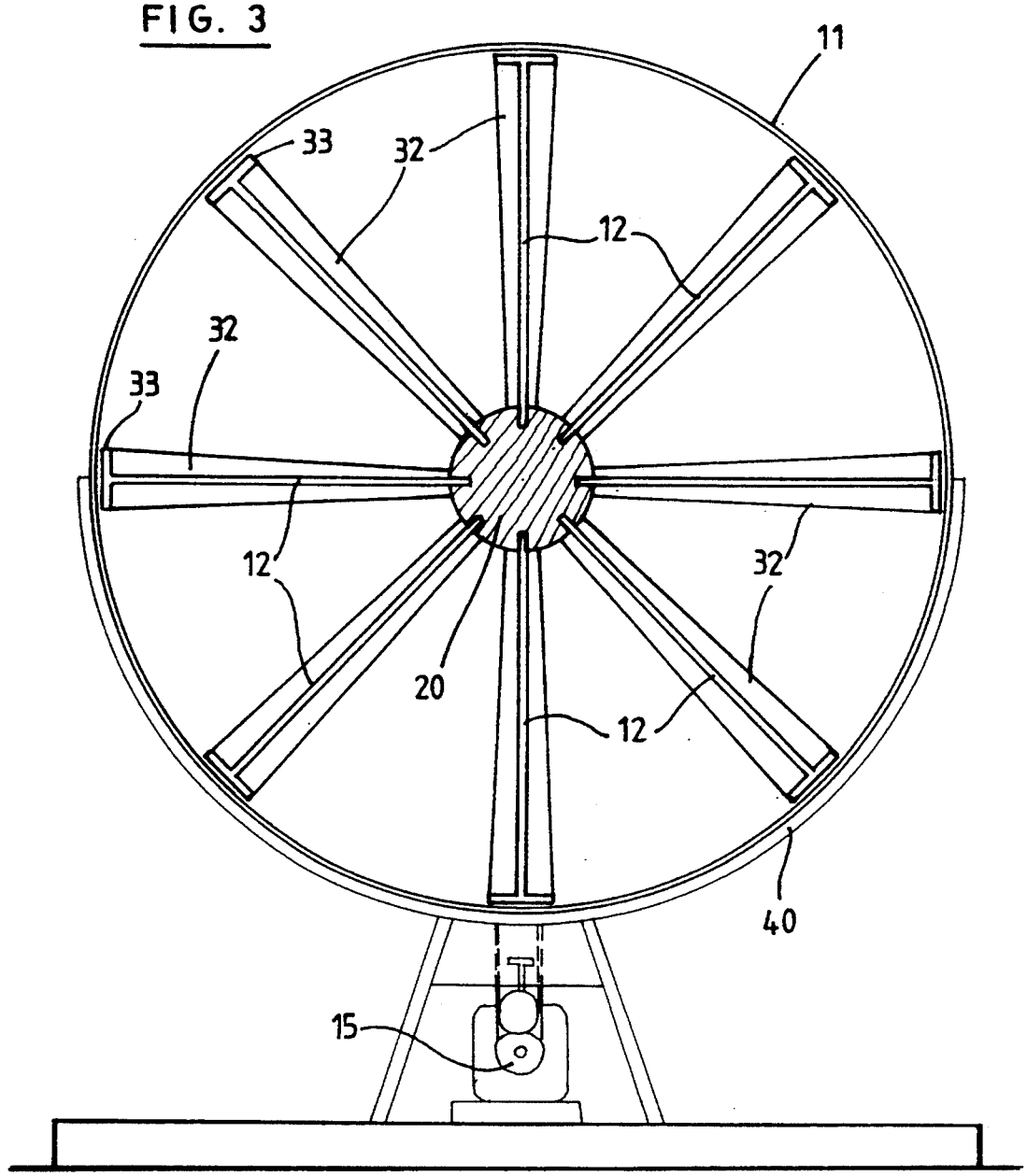

APPARATUS HAVING ROTATABLE PLANAR TRAYS FOR CULTURING MICROORGANISMS

FIELD OF THE INVENTION

The invention relates to an apparatus for developing a reactive exchange surface which is renewed regularly between a liquid phase and a gas phase. An apparatus of this type is intended, for example, for cell culture and the production of biological substances.

BACKGROUND OF THE INVENTION

In industries producing vaccines by means of cell culture or producing biological substances secreted either by adherent or suspension cells or by microorganisms, use is made of microcarriers, roller bottles, Roux flasks, multiple chamber systems and fermentors.

Microcarriers are small microscopic beads on which adherent cells are caused to grow. The beads are maintained in suspension in the culture medium, hereafter called the liquid phase, with the help of a stirring system, the liquid phase being in contact with a gas phase. Everything is contained in a tank called fermentor. This technique frequently used in the vaccine industry is nonetheless confronted with two major difficulties:

the difficulty of carrying out a suspension of microcarriers in the culture medium which is compatible with anchorage and cell growth conditions, the difficulty of ensuring the control and stability of the culture medium pH, when taking into account the fact that the exchange surface between the gas phase and the liquid phase is substantially limited.

Fermentors are also used for the culture of suspension cells or micro-organisms. The handling difficulties are similar to those encountered during cultivation with a microcarrier; as the exchange surface between the gas phase and the liquid phase is limited by the fermentor diameter, the pH stability becomes extremely difficult to ensure.

Roller bottles are generally of cylindric shape and are designed to be rotatable around their axes. The interior surfaces of these bottles are foreseen for cultivating adherent cells thereby forming culture surfaces. The liquid of culture is introduced into the bottle together with the cells. The rotating movement to which the bottles are subject, allows the culture surfaces to be covered with a film of medium thereby allowing cell growth on these culture surfaces. The culture surface is therefore limited to the size of the bottles. If the production of a large quantity of cells is desired, a large number of bottles will be necessary. This is the case for industries producing, for example, interferon, insulin, viral vaccines, lymphokines. The handling of these numerous bottles during inoculation, medium change, virus introduction, supernatant and cell harvesting increases the risk of bottle and content contamination and requires the use of an important number of staff. Many apparatus have been developed in order to increase the culture surface of roller bottles by increasing the surface of the bottle itself. These known apparatus are intended for developing adherent cell culture but are not foreseen for providing a homogeneous suspension of microcarriers or of suspension cells.

Roux flasks have been used for more than a century for producing viruses, as well as other biological substances. They have the same drawbacks as roller bottles, that is to say a limited culture surface per bottle and they require an important number of handling staff.

Document EP-A-0345415 discloses an apparatus in which the bottle has an enlarged surface. This enlargement of the surface is obtained by providing the bottle body with a corrugated surface having corrugations which extend axially or longitudinally relative to the bottle axis. This bottle does not, however, allow liquid stirring. Therefore it does not permit cultivation with microcarriers.

The surface used for cell development is also increased with the apparatus disclosed in document U.S. Pat. No. 3,839,155. With this apparatus, additional surface is obtained with a parallel arrangement of trays along the bottle axis. This apparatus however is not entirely satisfactory for adherent cells because the trays, when in a horizontal position, cannot retain a volume of liquid containing the cell suspension. This causes the liquid to run out of the tray which does not favour cell attachment during cultivation. Moreover, this apparatus is not appropriate for the cultivation of so-called non-adherent cells because nothing is provided here for stirring of the liquid phase.

Document LU-A-51646 describes a cell culture apparatus comprising Of a set of parallel trays placed one above the other so as to form culture chambers. All of this is placed inside the housing which can be rotatable around an axis. This system permits cultivation of adherent cells on one side of the trays only. The interior surface of the housing is not used as a culture surface. Moreover, a stirring system allowing the microcarriers or micro-organisms to be maintained in homogeneous and continuous suspension, cannot be introduced.

SUMMARY OF THE INVENTION

The present invention aims to remedy these drawbacks. To this end, there is provided an apparatus comprising of an elongated closed housing defining a volume for a reaction liquid, a device for introducing the reaction liquid into the housing and also for removing it therefrom and at least one set of trays arranged longitudinally inside the housing with a regular spacing therebetween, the set of trays being mounted for rotation in such a way as be able to turn around a longitudinal axis, driving means to drive the set of trays in rotation in at least one direction around the aforementioned longitudinal axis, the said trays having along their edges, rims which protrude from at least one of the opposite sides of the trays in such a way as, during the rotation of the aforementioned set of trays, the trays dip successively into the reaction liquid and each retain a predetermined quantity of liquid during a part of their angular travel.

Therefore, owing to the layout of the proposed trays, according to the invention, the exchange or culture surface is considerably increased for equal volumes and the Setting in suspension of non adherent cells, microorganisms, microcarriers or microspheres is ensured without having to use any internal stirring system. The rotation of the trays provides excellent stirring of the liquid phase introduced into the apparatus by the liquid being carried along by the rotating trays.

This stirring and the liquid movement within the housing which are obtained due to the rotation of the trays provides a homogeneous distribution of the liquid phase elements and greatly increases the exchange and culture efficiency.

The trays can be laid out and fixed in various ways. In an exemplary embodiment the trays are arranged radially around an axis which extends longitudinally inside the housing and which are fixed to the said axis or to the internal surface of the housing or even both to the axis and the internal surface of the housing. The trays are advantageously made removable and slidable for example into grooves provided for receiving their longitudinal edges. The sides of the trays can be corrugated, which further increases the development and yield of the exchange or culture surface.

Another interesting embodiment, because it is relatively easy to construct, comprises of a set of parallel trays assembled in such a way as to present regular spacings between each other. In this way also, the trays can be fixed together to form a rotating body inside the housing or be mounted to the lining of the housing, for example by sliding them into grooves provided on the interior surface of the housing.

Various other details of embodiment of the apparatus according to the invention are defined in the subclaims.

In an advantageous manner, the invention provides rotating the trays alternately at least a half turn in one direction and then in the other in order to obtain excellent wetting of the opposite sides of the trays with a film of reaction agent.

The invention is described in further detail hereafter, by way of example, with reference to the appended drawings representing a few preferred embodiments.

BRIEF DESCRIPTION OF THE DRAWINGS

FIG. 3 is a cross-sectional view of a second embodiment according to the invention.

In the drawings, identical reference numerals designate parts or elements which are identical or similar and equivalent.

DESCRIPTION OF PREFERRED EMBODIMENTS

Generally, an apparatus according to this invention consists of an elongated closed housing which defines a volume for a liquid of reaction and a set of trays arranged longitudinally inside the housing with a regular spacing between them. The set of trays is mounted to be rotated in such a way as to turn around a longitudinal axis thanks to any driving means, known per se. Along their sides, the trays have raised rims which protrude from one side or from the two sides of each tray in such a way as to act as a retainer element for the liquid of reaction into which the trays are dipping one after the other during their rotation.

Herein after there will be described by way of example an apparatus called rotating bioreactor intended to allow the culture of adherent or non adherent cells with or without microcarriers or the culture of bacteria and other micro-organisms. To this end, if it is for adherent cell culture, for example, a liquid is introduced into the bioreactor housing to breed and grow the cells and micro-organisms on the opposite sides of the trays and on the internal wall of the housing. In order to enhance culture performance, it is necessary to increase the available surface susceptible of entering into contact with the reactive liquid and equally to maximize its exploitation.

Figure 1:
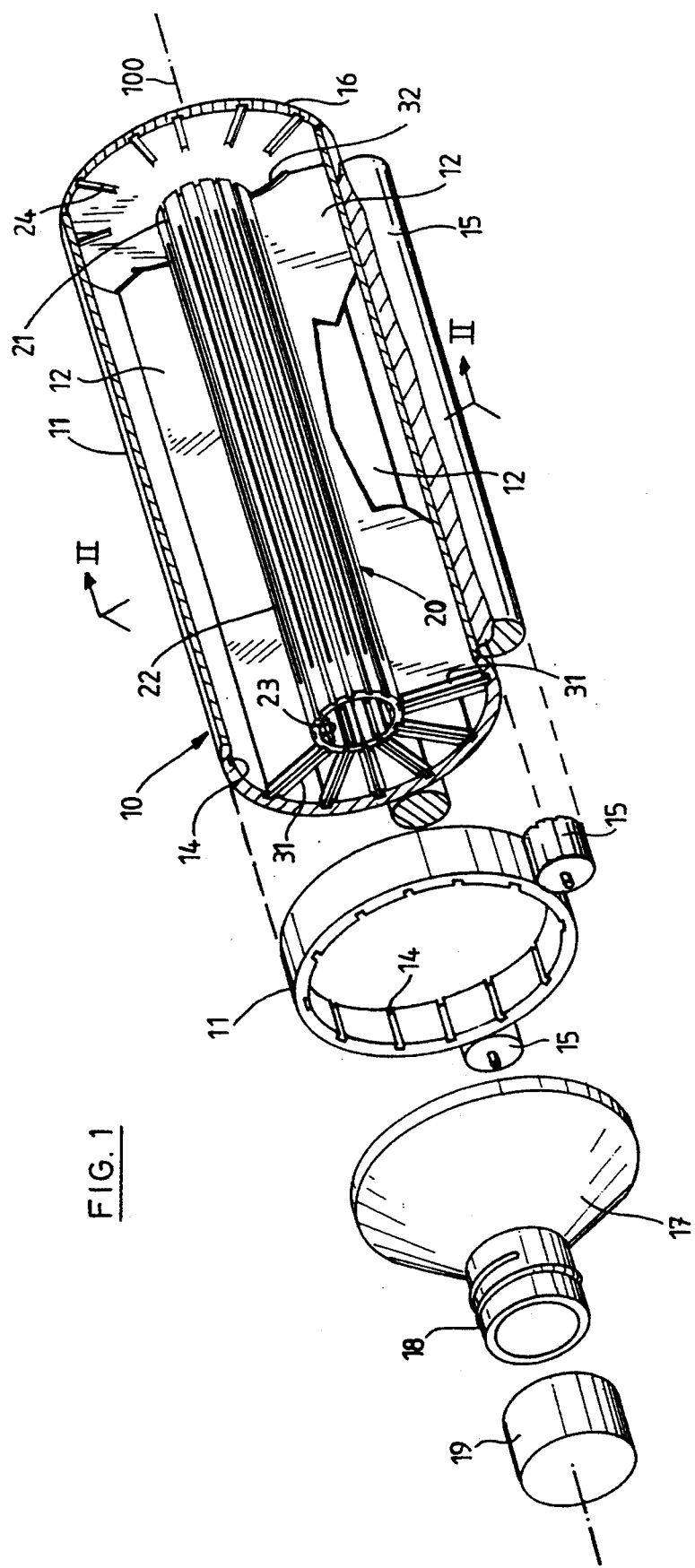
FIG. 1 represents a perspective view, partially broken away, of a first embodiment in accordance with this invention, in which the trays are arranged radially.
Figure 2:
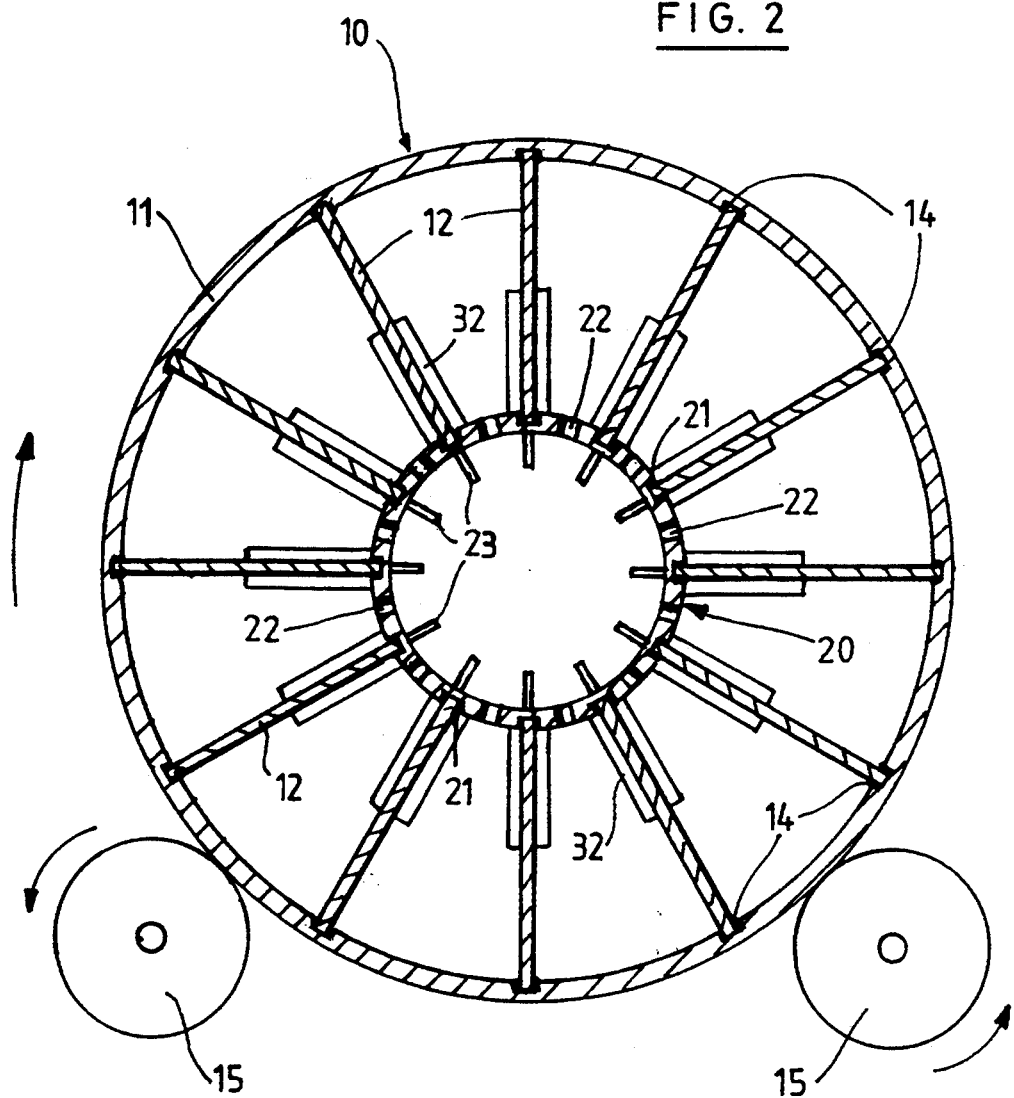
FIG. 2 represents on an enlarged scale, a cross-sectional view along line II—II in FIG. 1.

The exemplary embodiment illustrated in FIGS. 1 and 2 shows a rotating bioreactor 10 in the shape of a flask comprising an external cylindrical housing 11, mounted on rollers 15 which are to be driven into rotation around its longitudinal axis 100. At its opposed ends, the housing 11 has a base 16 and a neck 17. The neck has a bottle neck 18 which extends concentrically to the longitudinal axis 100 of the housing and which serves to accommodate a closing means such as a screw cap 19. Inside the housing, the trays 12 are arranged radially at regular intervals around an axis 20 which extends longitudinally inside the housing. The trays 12 extend substantially the whole length of the housing up to a predetermined distance from the aforementioned base 16 and neck 17. The trays 12 may however be also shorter in length. These trays 12 which have a substantially rectangular shape, are normally rigid so that they can support their own weight as well as the weight of the liquid which they are intended to retain as will be apparent later herin. Their number can vary as a function of the technical characteristics of the apparatus.

In the embodiment illustrated in FIGS. 1 and 2, the trays extend from the axis 20 to the housing 11 and are fixed at their two opposite ends, respectively to the axis 20 and to the housing 11. To this end, the inner surface of the housing 11 and the outer surface of the axis 20 have longitudinal grooves 14 and 21 respectively, arranged in such a way as to securely fix the trays. The aforementioned grooves 14 and 21 extend substantially the entire length of the housing 11 and of the axis 20.

The lateral edges 28 and 29 of each tray 12 are equipped with raised rims 31 and 32 which protrude from one side or from the two opposite sides of the tray. One portion of the lateral edge 29 intended to be at the base of the housing 11 is provided to rest on the base 16 and to fit into the radial grooves 24 provided in the inner side of the base 16. The other portion of the lateral edge 29 is curved and has a raised rim 32 which protrudes from the plane of the tray. The curvature allows the tray and the adjacent end of the axis 20 to be aligned during their mounting and provides a passage for the gases. The aforementioned raised rims may possibly have a height which is decreasing from the longitudinal side 26. Each tray together with the aforementioned raised rims substantially form a basin which is able to retain temporarily a determined quantity of the reactive liquid contained in the housing when each tray is dipping in turn in the reactive liquid during the entire rotation of the assembly and this through a portion of its ascending angular path.

The axis 20 is advantageously hollow and has parallel longitudinal openings 22 alternating with the grooves 21. The openings 22 allow the reactive liquid to flow inside the axis 20. During rotation of the trays, the liquid then covers ribs 23 provided on the inner surface of the axis 20. The reactive liquid then flows over the ribs 23 below, crosses the corresponding openings 22 and flows along the trays 12 underneath. Of course, the axis 20 could also be solid instead of being hollow.

The trays generally have a planar surface. However, they can also have a slightly warped or out of true shape. With the aim of enlarging the total culture surface of each tray, the trays sides are provided with corrugations, e.g. stripes. This further increases the development of the reaction or exchange surface and makes cell or micro-organism culture very efficient.

The inner surface of the housing 11 as well as each of the opposite sides 25a and 25b (see FIGS. 4 and 5) of the trays 12 are treated for cell culture either before assembling, during partial assembling or even when the apparatus is completely assembled and this with the purpose of obtaining an optimal surface treatment compatible with the nature of the substance or micro-organism to be stuck or cultivated.

When assembling the apparatus, before hermetically attaching the base 16 to the housing 11, the trays 12 and the axis 20 are slid inside the housing 11 so that the trays fit into the grooves 21 of the axis 20 and into the longitudinal grooves 14 of the housing 11. The foregoing is a description of one way of assembling the apparatus only. The trays can also be fitted by sliding them into their respective grooves 14, 21, 24 provided on the housing 11, on the axis 20 and on the base 16. Here it is the neck 17 which is hermetically attached to close the housing. When the trays 12 have been placed inside the housing 11, it is then closed by attaching the neck 17.

The reaction agent and the substances to be cultivated are introduced through the bottle neck 18 of the housing placed, for example, vertically by means of a device, known per se, serving to introduce the reaction agent. The filling up of the housing can equally be done when same is placed horizontally. In this case, it is one or more tubes (not shown in the drawings) placed in the neck extending either along the axis of the housing 11 or along the inner surface of the neck which allow liquids or gases to be introduced or drained or allow the contents to empty the housing without having it to be opened.

In the example described above, the trays 12 are attached at their two longitudinal edges. It must be noted that the trays 12 can be attached at only one of their longitudinal edges, either by having one edge only attached to the axis 20, or by having one edge only attached to the housing 11. In the first case the axis 20 and the trays 12 which it carries form an assembly mounted in such a way as to be driven into rotation inside the housing. FIG. 3 represents an example of embodiment in which the trays 12 are attached to the axis 20 which, here, is a solid axis. The trays fit into grooves provided longitudinally in the external surface of the axis. This is mounted inside the housing 11 supported by a framework 40. The free longitudinal edge of each tray 12 has a longitudinal raised rim 33 which protrudes from the sides of the tray. The tray with the longitudinal raised rim 33 and the aforementioned lateral raised rims form a basin capable of retaining a quantity of reaction liquid as explained above. The axis 20 is coupled through a transmission device to a driving motor 15 so that the set of trays can rotate around the longitudinal axis of the housing. The latter could also accomodate several sets of trays capable of rotating around parallel axes.

Figure 4:
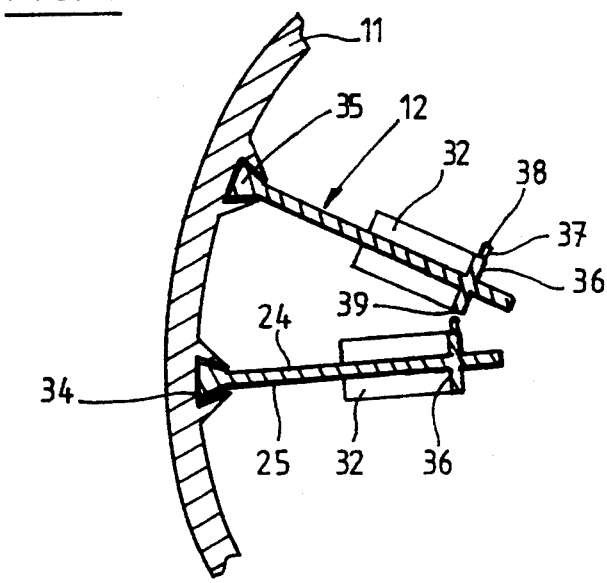
FIG. 4 is a partial cross-sectional view of a third embodiment according to the invention.

In the case where the trays are solely attached to the housing, the latter drives the trays into rotation around the longitudinal axis of the housing. FIG. 4 illustrates an example of embodiment in which the trays are attached to the housing. The trays 12 are attached by means of mortised dovetail shaped tongues 34 allowing to slidably receive the dovetail shaped tenon 35 formed along the external longitudinal edge 26 of the tray 12. This way of attaching the trays proves very secure and particularly appropriate when important masses of liquid need to be entrained along while ensuring an easy interchangeability of the trays, which can prove useful for replacing them in case of tray alteration.

Figure 5:
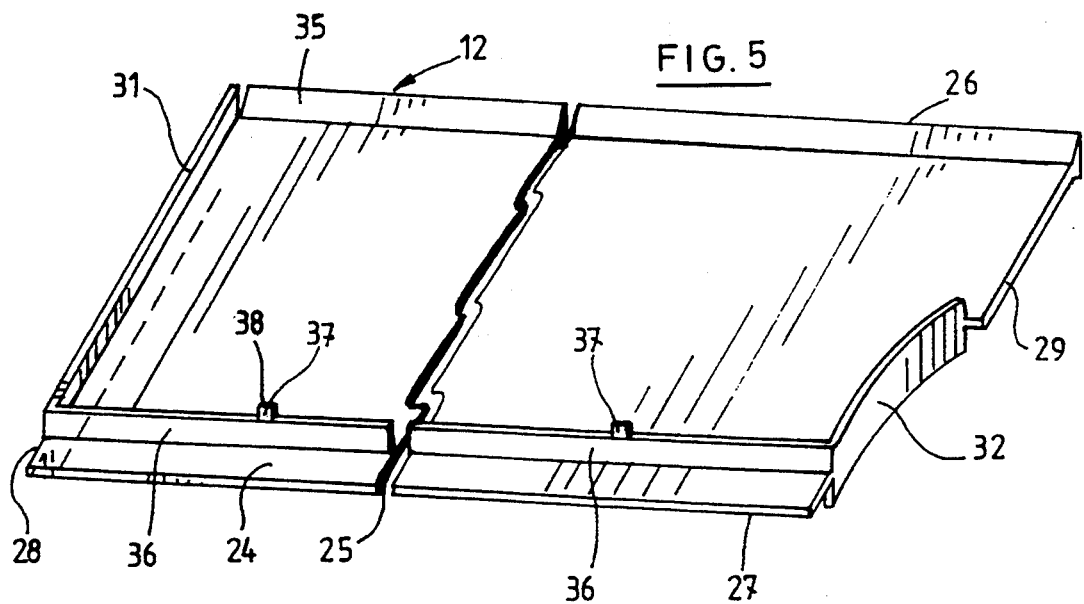
FIG. 5 is a perspective view of an exemplary tray of the apparatus according to FIG. 4.

On its opposite sides 25a and 25b, each tray 12 has a partition 36 placed longitudinally along the free longitudinal edge 27 of the tray, possibly throughout the length of the tray 12. FIG. 5 shows a perspective view of such a tray layout. The longitudinal partition 36 and the lateral rims 31 and 32 mentioned earlier herein substantially form with the tray a basin capable of momentarily retaining a determined quantity of reaction liquid through the ascending angular path of the tray. In order to avoid that the free edges of the adjacent trays touch each other in the event that the trays come to bend under the weight of the retained liquid or under the effect of vibrations, the longitudinal partitions 36 have at their edge at least one protruding element 37 which serves as a spacer and which provides a resting surface 38 for the edge 39 of the adjacent partition 36 placed on the adjacent tray 12, thereby to always ensure a spacing between two next adjacent trays and to allow the free passage of gases and the flow of liquids during rotation of the trays.

The trays edges can also be of other shapes such as, for example, at least one plain edge without any perpendicularly raised rim, an edge with a lip or an edge for entirely resting on the base 16 of the housing 11. The lateral rims and the longitudinal partitions have advantageously the same height in their adjoining area. The lateral rims have possibly a height which is decreasing regularly from the longitudinal edge 26 to the longitudinal edge 27 of the tray.

When an appropriate quantity of liquid and gas is introduced into the housing 11, the latter together with the trays 12 or the trays 12 alone are driven into rotation around the longitudinal axis of the housing under the action, of driving means 15 provided to this purpose. During their rotation, the trays 12 are dipping in turn into the reaction liquid and during the ascending travel of the trays, a determined quantity of reaction liquid is retained by the rims of each tray and is entrained along with the trays. The liquid in excess flows gradually over the rims and then through the openings 22 in the axis 20 or, possibly, through the space between two adjacent partitions 36 of next adjacent trays (in the case of the embodiment of FIG. 4). The liquid falls again to the lower part of the housing and covers all the surfaces lower down.

A rotation through at least 180° in one direction, followed by a rotation through at least 180° in the opposite direction after return to the starting point, allows a film of reaction agent to "wet" the opposite sides 25a, 25b of the trays 12 and the interior surfaces of the housing and to cultivate adherent cells on these surfaces.

Figure 6:
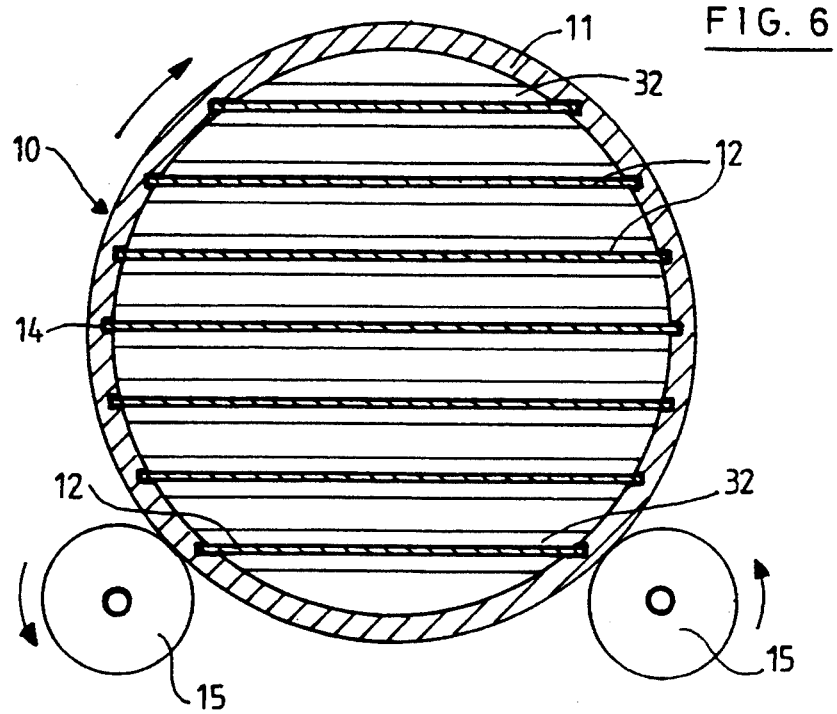
FIG. 6 represents a cross-sectional view of a fourth embodiment according to the invention, in which the trays are fitted in parallel arrangement.
Figure 7:
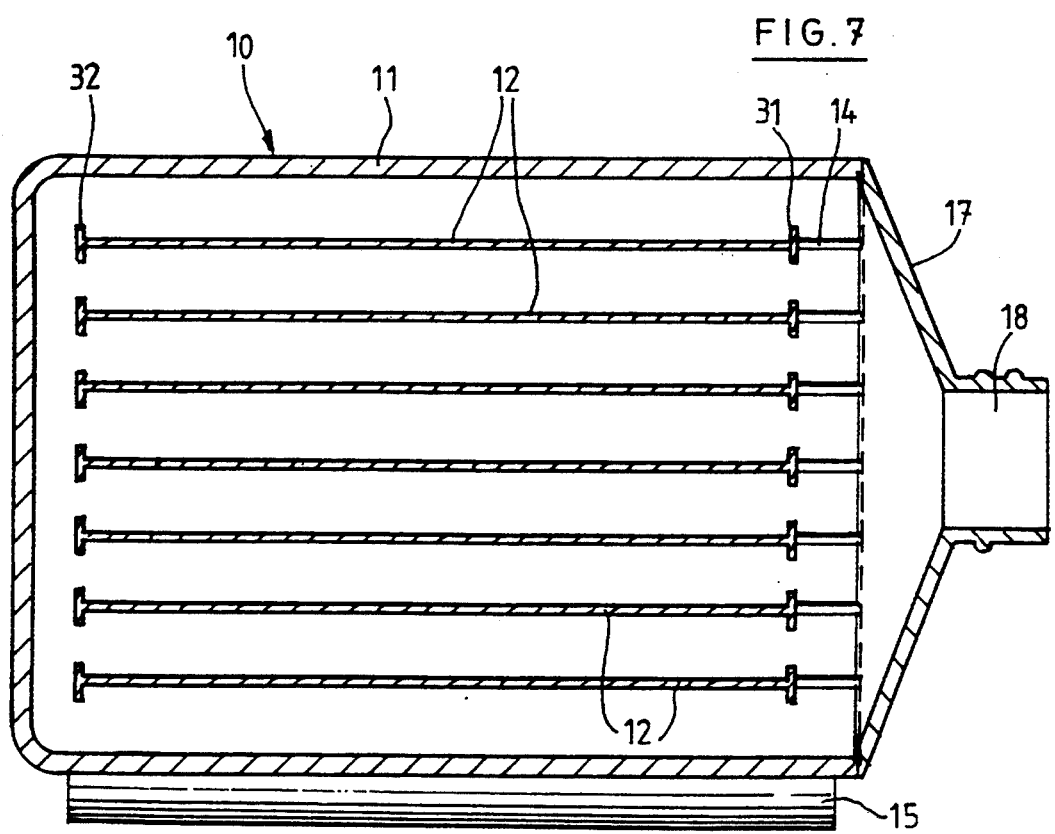
FIG. 7 is a longitudinal sectional view of the apparatus according to FIG. 6.

FIGS. 6 and 7 illustrate another way of arranging the trays. These are mounted parallel to each other following the direction of the longitudinal axis of the housing and they are attached to the housing 11 at their two opposite longitudinal edges.

The trays can also be attached to the housing 11 at one longitudinal edge only or attached together with a regular spacing therebetween to form a rotatable assembly. In the case where the trays are attached at one edge only, an advantageous arrangement consists in providing an alternate attachment by successively fitting one longitudinal edge of the tray, then the opposite longitudinal edge of the next adjacent tray. The parallel arrangement of trays proves to be particularly simple to construct.

When adherent cells are cultivated within the housing, they can be harvested using conventional methods such as a proteolytic enzyme solution, e.g. trypsin, versen or any other chelating agent which aims to detach cells from their support.

The rotating bioreactor is designed to allow equally culture of adherent cells as well as suspension cells. it also allows adherent cell culture with micro-carriers. In this case, all the inner surfaces provided to this end and the surface formed by the microcarriers can be used for cell growth.

Rotating the trays through half a turn in one direction and then in the other direction makes it possible to connect several apparatus together while working. To this end, an orientation mark is advantageously provided on each apparatus, e.g. a reference mark, so as to ensure a well coordinated operation of the different apparatus. This allows, with the help of tubes as mentioned above, to introduce or drain liquid at any time, to change medium without having to open the housing and to take representative microcarrier samples in order to observe cell growth.

The apparatus according to the invention permits two types of culture to be carried out within a same bottle, viz adherent cell or micro-organism culture or non-adherent cell or micro-organism culture, with or without microcarriers. This significant and specific advantage of the invention thus allows only one type of bottle to be used, whatever the type of cells or microorganisms cultivated may be.

The arrangement of several trays makes it possible to substantially increase the culture surface for a constant volume. Thus, the apparatus permits the production of a large quantity of cells in a restricted total volume.

It is therefore apparent that the apparatus according to the invention permits both the culture surface and the exchange surface between the liquid and gas phases to be substantially increased within a given volume. The increase in surface as compared to a conventional roller bottle or a fermentor can be higher than 1000%.

Another advantage of the apparatus according to the invention is that the culture conditions are kept independent from the size of the housing, the ratio between the volume of liquid used, the volume of the gas phase and the total culture or exchange surface being constant. The changeover from a low capacity housing to a housing of a greater capacity can therefore be done without modifying the parameters ruling the culture.

The apparatus also permits a liquid phase to be concentrated by evaporation. The large exchange surface between the gas phase and the liquid phase allows, by circulating dry gas inside the housing or by sucking up the gas phase, to partially or entirely evaporate the liquid phase contained in the housing.

The embodiments of the invention described in the foregoing are examples given by way of illustration and the invention is by no means limited to these examples. Any modification, any variation and any equivalent arrangement should be considered as being comprised within the scope of the invention.

I claim:

1. An apparatus for culturing microorganisms within a reaction liquid medium, comprising a closed elongated housing defining a volume to receive a reaction liquid and a volume for a gas phase, the housing being comprised of a substantially cylindrical body elongated along a longitudinal axis and being closed at one end by a base and at the other end by a closing cap for introducing the reaction liquid into the housing and for removing it therefrom, a set of planar trays arranged longitudinally to said longitudinal axis inside the housing having their longitudinal edges attached to the housing and extending in parallel to one another with a regular spacing between them, the trays having along their edges rims which protrude from both opposite planar sides of the trays for at least momentarily retaining reaction liquid thereon, driving means to impart a rotating movement to the housing and set of trays such that, when the set of trays is rotated through a path of angular travel, the trays dip into the reaction liquid and retain a predetermined quantity of liquid momentarily on the planar sides of the trays to cultivate cells thereon during a part of its angular travel.

2. The apparatus according to claim 1, wherein each tray is attached to the housing at one of its longitudinal edge.

3. The apparatus according to claim 1, wherein the trays have corrugations on substantially the whole surface of one of their opposite planar sides.

4. The apparatus according to claim 1, wherein the trays are removably attached to an inner surface of the housing.

5. A method of culturing microorganisms in an apparatus comprising a closed elongated housing defining a volume to receive a reaction liquid and a volume for a gas phase, the housing being comprised of a substantially cylindrical body elongated along a longitudinal axis and being closed at one end by a base and at the other end a closing cap for introducing the reaction liquid into the housing and for removing it therefrom, a set of trays arranged longitudinally to said longitudinal axis inside the housing having their longitudinal edges attached to the housing and extending in parallel to one another with a regular spacing between them, the trays having along their edges rims which protrude from both opposite planar sides of the trays for at least momentarily retaining reaction liquid thereon, and driving means to impart a rotating movement to the set of trays, said method comprising the steps of:

(a) introducing a reaction liquid medium into said housing, (b) causing the housing and set of trays to rotate through 180° in a first direction about the longitudinal axis of the elongated housing, (c) causing the housing and set of trays to rotate through 180° in a second direction opposite to said first direction about the longitudinal axis of the elongated housing, whereby rotation of the trays through 180° in alternate directions allows them to dip into the reaction liquid and retain a predetermined quantity of liquid momentarily on each planar side of the trays in each direction of rotation to thereby cultivate cells on both planar sides of the trays; and (d) repeating the steps (b) and (c).

* * * * *